United States Patent [19]

Rovnyak

[11] 4,371,543
[45] Feb. 1, 1983

[54] BIS-AMIDINE INDENE KETONES, COMPOSITIONS CONTAINING SAME AND METHOD OF USE

[75] Inventor: George C. Rovnyak, Hopewell, N.J.

[73] Assignee: E. R. Squibb & Sons, Inc., Princeton, N.J.

[21] Appl. No.: 270,775

[22] Filed: Jun. 5, 1981

[51] Int. Cl.³ .............. A61K 31/155; A61K 31/195; C07C 123/00
[52] U.S. Cl. .................... 424/319; 424/326; 562/440; 564/243
[58] Field of Search ............... 564/243; 424/326, 319; 562/440

[56] References Cited

U.S. PATENT DOCUMENTS

| | | | |
|---|---|---|---|
| 2,395,471 | 2/1946 | Ewins | 564/243 |
| 4,078,086 | 3/1978 | Winkelmann et al. | 424/326 |
| 4,086,244 | 4/1978 | Sprague | 564/243 |
| 4,108,894 | 8/1978 | Sprague | 564/243 |

OTHER PUBLICATIONS

"Synthese von α,α-Bis-[amidinobenzyliden]-undα,α'-Bis-[amidinobenzyl]-cycloalkanonen", Wagner et al., Pharmazie 32, pp. 141–145 (1977).

*Primary Examiner*—Natalie Trousof
*Assistant Examiner*—L. Hendriksen
*Attorney, Agent, or Firm*—Lawrence S. Levinson; Burton Rodney

[57] ABSTRACT

Bis-amidine indene ketones are provided having the structure

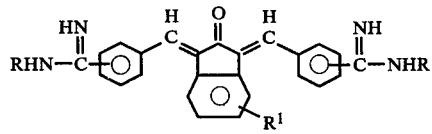

wherein R is hydrogen, lower alkyl or aryl; and $R^1$ is hydrogen, lower alkyl, halogen, carboxy, trifluoromethyl, lower alkoxy, hydroxy or acyl, and acid-addition salts thereof. In addition, pharmaceutical compositions containing the above compounds and a method of using same to treat inflammatory conditions in mammalian species are also provided.

8 Claims, No Drawings

BIS-AMIDINE INDENE KETONES, COMPOSITIONS CONTAINING SAME AND METHOD OF USE

FIELD OF THE INVENTION

The present invention relates to bis-amidine indene ketones, anti-inflammatory compositions containing same, and to a method for treatment of inflammatory conditions employing the above compounds.

DESCRIPTION OF THE INVENTION

The bis-amidine indene ketones of the invention have the following formula

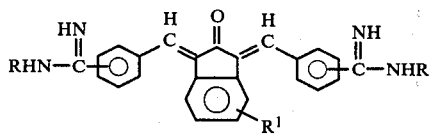

wherein R is H, lower alkyl or aryl and $R^1$ is H, lower alkyl, halogen, lower alkanoyl, aroyl, carboxy, lower alkoxy, hydroxy or trifluoromethyl.

The compounds of Formula I will preferably be in the form of their acid-addition salts with inorganic and organic acids. Illustrative of such acid salts are the hydrohalides, especially the hydrochloride and hydrobromide which are preferred, sulfate, nitrate, phosphate, borate, acetate, tartrate, maleate, citrate, succinate, oxalate, benzoate, ascorbate, salicylate, methanesulfonate, benzenesulfonate, toluenesulfonate and the like.

Preferred are those compounds of Formula I wherein R is H or lower alkyl, $R^1$ is hydrogen or lower alkyl in the meta-position on the benzene portion of the indene ring, and the

group is in the meta- or para-position of each of the phenyl groups, in the form of their hydrohalide salts, especially the HCl salt.

The terms "lower alkyl" and "lower alkoxy" as used throughout the specification (by themselves or as part of a larger group) refer to groups having 1 to 8 carbon atoms. Alkyl and alkoxy groups having 1 to 3 carbon atoms are preferred.

The term "aryl" as used throughout the specification (by itself or as part of a larger group) refers to phenyl or phenyl substituted with a lower alkyl, lower alkoxy, halogen or trifluoromethyl group. Phenyl is the preferred aryl group.

The term "halogen" as used throughout the specification refers to fluorine, chlorine, bromine, and iodine; fluorine and chlorine are preferred.

The term "lower alkanoyl" as used herein refers to a radical of the structure

wherein $R^2$ is lower alkyl as defined above.

The term "aroyl" as employed herein refers to a radical of the structure

wherein $R^3$ is aryl as defined above.

The Formula I compounds of the invention are prepared by condensing an amidino benzaldehyde II with a ketone III employing a molar ratio of II:III of from about 2:1 to about 4:1, preferably from about 2.0:1 to about 2.5:1, and optimally about 2:1, using acid catalysis. Although the condensation proceeds in hot (about 100° C.) 85% $H_3PO_4$ and the product can, after isolation, be converted to the hydrohalide salt, the preferred conditions for preparing the compounds of Formula I involve heating the reactants II and III in 5–10% aqueous mineral or other acid, preferably hydrochloric acid, at reflux temperature for one to eight hours, preferably one to four hours. The product I in the form of the amidine acid-addition salt is collected from the cooled solution and can be recrystallized, if necessary, for example, from 0 to 5% aqueous hydrochloric acid

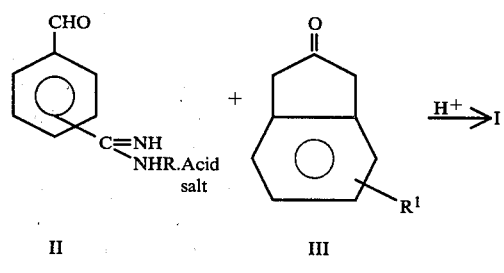

wherein R and $R^1$ are as defined above with respect to the Formula I compounds.

The amidine acid-addition salt may be converted to the free base I of the invention as follows.

The amidine acid-addition salt I, dissolved or suspended in water, is treated with an excess of 10% aqueous sodium hydroxide at or below room temperature and extracted several times with chloroform. The organic extracts are washed with saturated brine, dried over anhydrous magnesium sulfate and concentrated in vacuo to give the free base. If necessary, the free amidine base can be recrystallized from a suitable solvent (e.g., ethanol, dioxane, benzene, carbon tetrachloride and combinations thereof).

The amidino benzaldehyde II may be prepared by methods reported in East German Pat. No. 109,864 and Pharmazie, 32, 39 (1977). These methods proceed through the intermediate iminoether acid salt, such as hydrochloride IV. In Method A, the iminoether acid salt (hydrochloride) IV is converted to the amidino benzaldehyde II (where R is H) with aqueous methanolic ammonium chloride. In Method B, the iminoether acid salt, such as the (hydrochloride) IV is initially converted to ketal V with triethylorthoformate in methanol. The ketal V is converted to amidine VI with the appropriate amine $NH_2R$ in methanol and the amidine VI is transformed to the amidino benzaldehyde II with aqueous methanolic hydrochloric acid or other acid. Method B is preferred because it allows for the introduction of different R groups

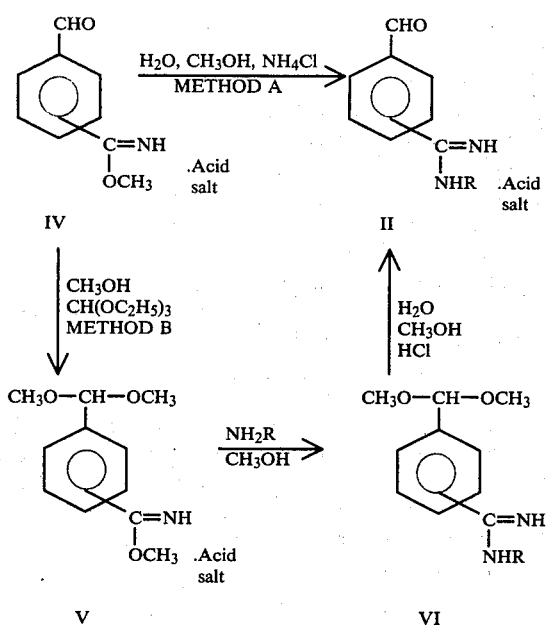

The ketones of Formula III are prepared by known literature methods as described in Org. Syn., 41, 53 (1961), Tet. Let., 1863 (1977), U.S. Pat. No. 4,128,666, J. Med. Chem., 13, 1226 (1970), and Aust. J. Chem., 29, 2571 (1976).

Amidines are strongly basic compounds and react with acids to form salts, such as hydrochlorides, sulfates, sulfonates, acetates, nitrates, carbonates, etc. [S. R. Sandler and W. Karo, "Organic Functional Group Preparations", Vol. III, Chap. 6, Academic Press, New York (1972)].

The free base can be combined with an excess, preferably with 2.2 to 3.0 equivalents of the desired acid in an appropriate solvent, such as aqueous ethanol (or acetone, dioxane, etc.) to give the amidine acid-addition salt.

Alternatively, one amidine acid-addition salt may be converted to another acid-addition salt by mixing with an excess (at least 10-100 fold) of the second acid (or its sodium, potassium or ammonium salt) in an appropriate solvent. For example, the amidine hydrochloride can be mixed with an excess of sodium acetate in warm water (or appropriate solvent mixture) to give the amidine acetate upon cooling [J. Chem. Soc., 1996 (1949)].

The compounds of the invention have antiinflammatory activity as measured by the mouse active arthus (MAA) test (Goldlust, M. B., Harrity, T. W., and Palmer, D. M., "Evaluation of Anti-Rheumatic Drugs Using the Cutaneous Arthus Reaction," Recognition of Anti-Rheumatic Drugs, D. C. Dumonde and M. K. Jasani, MTP Press, Lancaster (1978), pp. 119–136), a Forssman anaphylaxis assay (a variation of the test described by Otterness, Ivan G., Torchia, Anthony J. and Doshan, Harold D., "Complement Inhibition by Amidines and Guanidines—In Vivo and In Vitro Results," Bio Chem. Pharm., Vol. 27, pp. 1873–1878 (1978)) and other related tests and are useful as antiinflammatory agents and are effective in the prevention and inhibition of granuloma tissue formation in warm blooded animals, and may be used, for example, in a manner similar to phenylbutazone or indomethacin. They may be used to decrease joint swelling, tenderness, pain and stiffness in mammalian species, such as dogs and monkeys, e.g., in conditions such as rheumatoid arthritis. Compounds of Formula I may be compounded for such use according to accepted pharmaceutical practice in oral dosage forms, such as tablets, capsules, elixirs or powders or in injectable form for administration of about 100 mg to 2 gm per day, preferably 100 mg to 1 gm per day in two to four divided doses.

The following Examples further illustrate and represent preferred embodiments of the invention. All temperatures are expressed in degrees Centigrade.

EXAMPLE 1

3,3′-[[2-Oxo-1H-indene-1,3(2H)-diylidene]bis(methylene)]bis[benzenecarboximidamide]

A. 3-Amidinobenzaldehyde hydrochloride

Ref: Wagner, Vieweg and Horn [Pharmazie, 32, 39 (1977)]

A solution of 3-cyanobenzaldehyde (30 g, 0.23 mole) in dioxane (90 ml), ether (33 ml) and methanol (22.2 g) is treated at 0° (ice bath) with 62 g of HCl gas under anhydrous conditions. Solvents are dried and the HCl gas is passed through two concentrated $H_2SO_4$ drying towers. After 24 hours at 0°–5° the reaction is filtered into 1400 ml of $Et_2O$. The solid that eventually forms is collected, washed with $Et_2O$ and dried in vacuo at 60° over KOH to give 40 g of the iminoether hydrochloride, m.p. 108°–110° (lit. m.p. 123°–5°).

The iminoether hydrochloride obtained above (6 g, 0.03 mole) is dissolved in ice water, made basic with 10% NaOH and rapidly extracted with $Et_2O$ (2×). The extracts are washed with saturated brine (2×), dried ($MgSO_4$) and concentrated in vacuo to give the free base (4.9 g). This is dissolved in MeOH (25 ml) and 10% aqueous $NH_4Cl$ (18 ml) and heated (100° oil bath) for 3 hours. Upon cooling, the mixture is poured onto $Et_2O$ (300 ml) and the oil that separates is collected and treated with acetone (300 ml). The supernatant is decanted from a tacky solid and concentrated in vacuo to remove all solvent, including residual water. The residue, upon trituration with fresh acetone, affords 3.2 g (57%) of product, m.p. 153°–7° (lit. m.p. 152°–4°).

B.
3,3′-[[2-Oxo-1H-indene-1,3(2H)-diylidene]bis(methylene)bis[benzenecarboximidamide]

A mixture of 2-indanone (1.22 g, 10 mmole) and 3-amidinobenzaldehyde hydrochloride (3.65 g, 20 mmole) in 25 ml of $H_2O$ and 3 ml of concentrated HCl is heated in an oil bath (120° to 140°) for 4 hours. Upon cooling, the product is collected and washed with dilute aqueous HCl, then 1:1 $H_2O$:acetone, acetone and $Et_2O$ to give 2.38 g m.p. 272°–3° d.

The combined filtrate and washing is concentrated to 25 ml and heated again at 120° (oil bath) for 2 hours. Crude product collected upon cooling is recrystallized from dilute aqueous HCl to give another 0.24 g product for a combined total of 2.62 g (66%).

EXAMPLES 2 to 12

Using the procedure described in Example 1 and employing the benzaldehyde derivative in Column I and the cyclic ketone derivative in Column II, there is obtained the product in Column III (Table I).

TABLE I

| Ex. No. | Column I | Column II | Column III |
|---|---|---|---|
| 2. | 4-CHO-C6H4-C(=NH)NHCH3·HCl | 5-Cl-indan-2-one (cyclopentanone fused) | 1,3-bis[4-(N-methylamidino)benzylidene]-5-chloro-indan-2-one ·2HCl |
| 3. | 3-CHO-C6H4-C(=NH)NHC6H5·HCl | 5-CH3-indan-2-one | 1,3-bis[3-(N-phenylamidino)benzylidene]-5-methyl-indan-2-one ·2HCl |
| 4. | 4-CHO-C6H4-C(=NH)NH-(3-CF3-C6H4)·HCl | 5-CO2H-indan-2-one | 1,3-bis[4-(N-(3-trifluoromethylphenyl)amidino)benzylidene]-5-carboxy-indan-2-one ·2HCl |
| 5. | 3-CHO-C6H4-C(=NH)NH2·HCl | 5-OCH3-indan-2-one | 1,3-bis[3-amidinobenzylidene]-5-methoxy-indan-2-one ·2HCl |
| 6. | 4-CHO-C6H4-C(=NH)NH-(4-Cl-C6H4)·HCl | 5-CF3-indan-2-one | 1,3-bis[4-(N-(4-chlorophenyl)amidino)benzylidene]-5-trifluoromethyl-indan-2-one ·2HCl |
| 7. | 4-CHO-C6H4-C(=NH)NHCH3·HCl | 5-OH-indan-2-one | 1,3-bis[4-(N-methylamidino)benzylidene]-5-hydroxy-indan-2-one ·2HCl |
| 8. | 4-CHO-C6H4-C(=NH)NHC2H5·HBr | 5-CO2H-indan-2-one | 1,3-bis[4-(N-ethylamidino)benzylidene]-5-carboxy-indan-2-one ·2HBr |
| 9. | 4-CHO-C6H4-C(=NH)NH2·HCl | 5-C2H5-indan-2-one | 1,3-bis[4-amidinobenzylidene]-5-ethyl-indan-2-one ·2HCl |

TABLE I-continued

| Ex. No. | Column I | Column II | Column III |
|---|---|---|---|
| 10. | CHO / C=NH·HCl / NHC6H5 (meta) | cyclopentanone fused with CH3-substituted ring | bis-imidamide product ·2HCl |
| 11. | CHO / C=NH·HCl / NHC6H5 (meta) | indanone | bis-imidamide product ·2HCl |
| 12. | CHO / C=NH·HCl / NH-C6H4-CH3 (meta) | CF3-substituted indanone | bis(tolyl-imidamide) product ·2HCl |

What is claimed is:

1. A compound of the structure

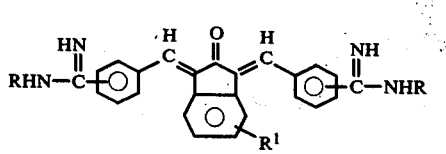

wherein R is H, lower alkyl or phenyl or phenyl substituted with a lower alkyl, lower alkoxy, halogen or a trifluoromethyl group, and R¹ is H, lower alkyl, halogen, carboxy, trifluoromethyl, lower alkyl, hydroxy, lower alkanoyl, or benzoyl or benzoyl substituted with a lower alkyl, lower alkoxy, halogen or a trifluoromethyl group, or acid-addition salts thereof.

2. The compound as defined in claim 1 wherein the  group is in the meta- or para-position.

3. The compound as defined in claim 1 wherein R is H or lower alkyl.

4. The compound as defined in claim 1 wherein R¹ is H or lower alkyl.

5. The compound as defined in claim 1 wherein R¹ is in the meta-position on the benzene portion of the indene ring.

6. The compound as defined in claim 1 having the name 3,3'-[[2-oxo-1H-indene-1,3(2H)-diylidene]bis(methylene)]bis[benzenecarboximidamide], or its hydrochloride salt.

7. An anti-inflammatory composition comprising a therapeutically effective amount of a compound as defined in claim 1 in a physiologically acceptable carrier therefor.

8. A method for treating an inflammatory condition in a mammalian host, which comprises administering an effective amount of the composition as defined in claim 7.

* * * * *